United States Patent [19]

Meller et al.

[11] Patent Number: 5,569,034

[45] Date of Patent: Oct. 29, 1996

[54] DENTAL HANDPIECE PROVIDING LOW SPEED, HIGH TORQUE ROTARY OUTPUT USING PLURAL STAGE PLANETARY GEAR REDUCTION

[75] Inventors: Moshe Meller, Princeton; Michael Feldman, Toms River, both of N.J.

[73] Assignee: MTI Precision Products, Inc., Lakewood, N.J.

[21] Appl. No.: 368,779

[22] Filed: Jan. 4, 1995

[51] Int. Cl.⁶ .............................. A61C 1/02; A61C 1/08; A61C 1/18

[52] U.S. Cl. .............................................. 433/105

[58] Field of Search ............................................. 433/105

[56] References Cited

U.S. PATENT DOCUMENTS

| | | | |
|---|---|---|---|
| 3,349,490 | 10/1967 | Lieb et al. | 433/105 |
| 4,040,311 | 8/1977 | Page, Jr. et al. | 433/105 |
| 4,433,957 | 2/1984 | Nakanishi | 433/105 |
| 5,281,138 | 1/1994 | Rosenstatter | 433/105 |

*Primary Examiner*—Nicholas D. Lucchesi
*Attorney, Agent, or Firm*—Frishauf, Holtz, Goodman, Langer & Chick

[57] ABSTRACT

A dental handpiece having a slow speed, high torque rotary output, comprises a housing member; an input shaft rotatably mounted in the housing member; a coupling member at an end portion of the input shaft for being coupled to a rotary dental drive unit; a plurality of planetary gear stages sequentially arranged within the housing member, a first of the planetary gear stages being coupled so as to be rotationally driven by the input shaft; subsequent planetary gear stages being sequentially coupled to each other such that an output of one planetary gear stage drives an input of a next subsequent planetary gear stage; and an output shaft coupled to a final output planetary gear stage of the plurality of sequentially arranged planetary gear stages. The output shaft provides a slow speed, high torque rotary output responsive to the input shaft being driven by a higher speed rotary dental drive unit.

19 Claims, 2 Drawing Sheets

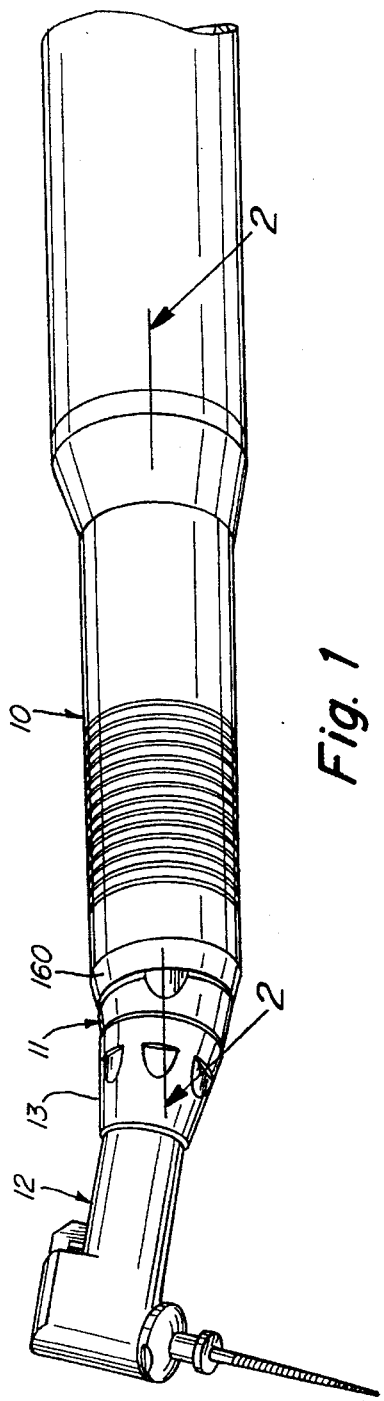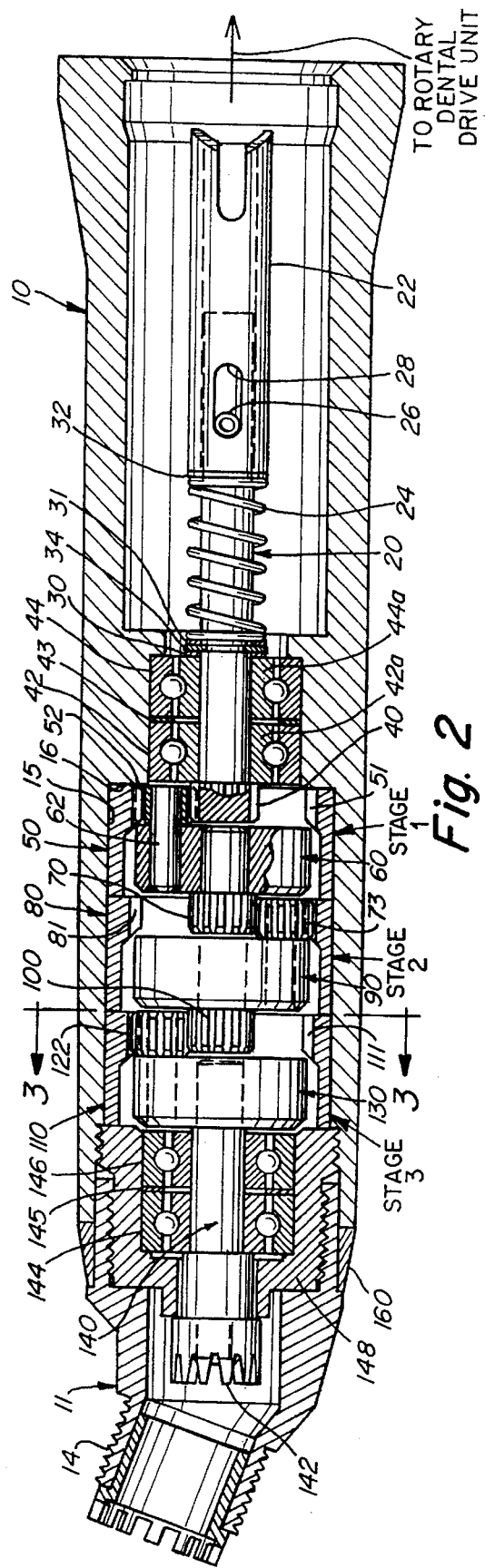

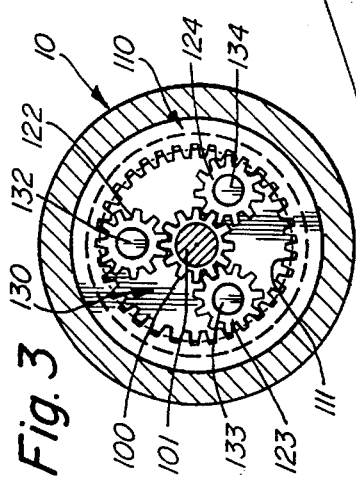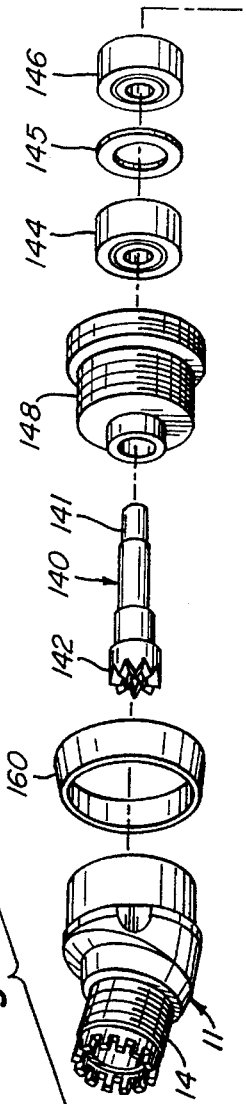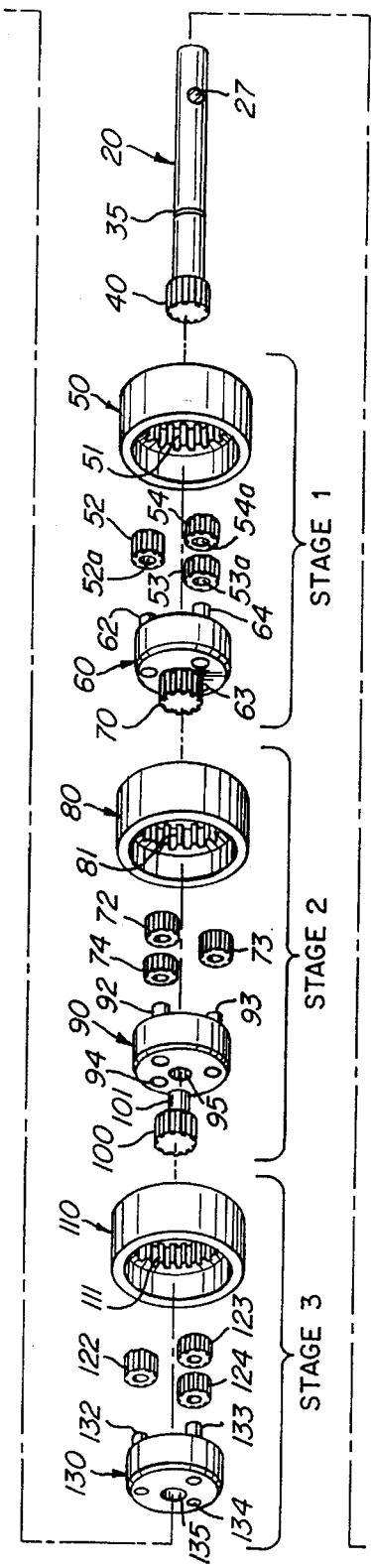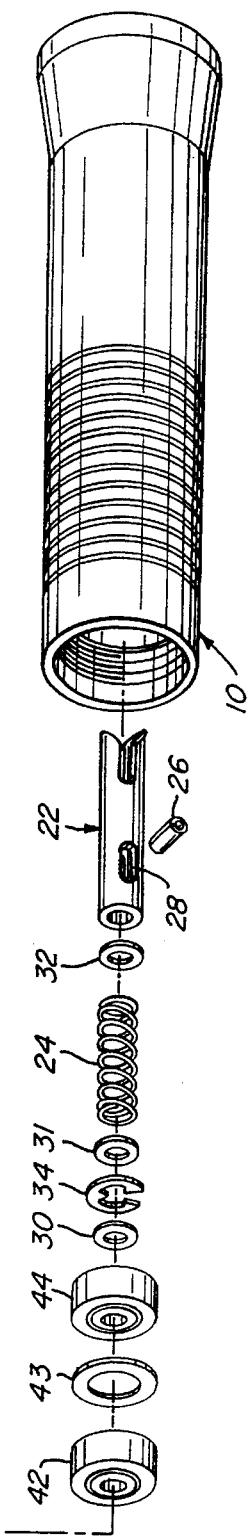

5,569,034

DENTAL HANDPIECE PROVIDING LOW SPEED, HIGH TORQUE ROTARY OUTPUT USING PLURAL STAGE PLANETARY GEAR REDUCTION

BACKGROUND OF THE INVENTION

This invention relates to a dental handpiece wherein the input drive speed is substantially reduced at the output thereof, and more particularly to such a dental handpiece using plural stages of planetary gears for reducing the output speed.

Dental handpieces providing slow speed, high torque, rotary output are used in various dental applications, such as in endodontic applications. When performing endodontic procedures, such as root canal therapy, various files or tapers (tapered files) providing a reaming action are installed on the dental handpiece, and are driven at a slow rotary speed with high torque. The presently available handpieces for providing such a slow speed, high torque rotary output are generally expensive and relatively complicated in design.

The object of the present invention is to provide a dental handpiece having a slow speed, high torque rotary output, which handpiece is simplified in design and construction, which is easily assembled, which can be driven by conventional dental drive sources, and which is therefore lower in cost.

SUMMARY OF THE INVENTION

According to the present invention, a dental handpiece having a slow speed, high torque rotary output, comprises a housing member; an input shaft rotatably mounted in the housing member, and having a coupling member at an end portion thereof for being coupled to a rotary dental drive unit; a plurality of planetary gear stages sequentially arranged within the housing member, a first of the planetary gear stages being coupled so as to be rotationally driven by the input shaft; subsequent planetary gear stages being sequentially coupled to each other such that an output of one planetary gear stage drives an input of a next subsequent planetary gear stage; and an output shaft coupled to a final output planetary gear stage of the plurality of sequentially arranged planetary gear stages, the output shaft providing a slow speed, high torque rotary output responsive to the input shaft being driven by the rotary dental drive unit.

According to a preferred embodiment each planetary gear stage provides a gear reduction of about 1:4.

BRIEF DESCRIPTION OF THE DRAWINGS

FIG. 1 is a perspective view of an assembled dental handpiece according to the present invention showing an endodontic tapered file mounted at the working end of the handpiece;

FIG. 2 is a cross-sectional view of the dental handpiece of FIG. 1, taken along line 2—2 in FIG. 1;

FIG. 3 is a cross-sectional view of the dental handpiece of FIG. 1, taken along line 3—3 in FIG. 2;

FIG. 4 is an exploded disassembled view showing the internal components of the dental handpiece of FIGS. 1–3.

DETAILED DESCRIPTION

Referring to the drawings, the dental handpiece of the present invention comprises a main housing member 10 having an output section 11 connected thereto. A contra-angle head 12 is connected to the output section 11 in a conventional manner, by means of a threaded collar 13 which threadably engages with threads 14 of the front end of output section 11. The dental handpiece of the present invention attaches at its input side to a conventional rotary dental drive unit (which usually is a pneumatic type of drive unit having, for example, an output drive speed of about 20,000 rpm) in a conventional manner, and attaches at its output side to a dental output member, such as the contra-angle head 12 shown in FIG. 1, also in a conventional manner.

The present invention resides in the construction of the drive mechanism interior of the main housing section 10 of the dental handpiece.

Referring to FIG. 2, an input drive shaft 20 has a coupling member 22 slidably mounted at the end portion of the drive shaft 20. The coupling member 22 interconnects with a conventional rotary dental drive unit which usually operates at a rotary drive speed of about 20,000 rpm so as to rotatably drive the drive shaft 20. A spring 24 biases the coupling member 22 in the right-hand direction as seen in FIG. 2, and the coupling member 22 is retained on the drive shaft 20 by means of a retaining pin 26 extending from the drive shaft 20 which is slidable in a slot 28 in the coupling member 22. Pin 26 is preferably press fit in a bore 27 (see FIG. 4) in drive shaft 20. Washers 30, 31, 32 are provided adjacent the opposite ends of the coil spring 24 to prevent binding of the apparatus during use. An E-clip 34 (see FIG. 4) is provided to retain the spring 24 assembled on the drive shaft 20. The E-clip 34 engages in a groove 35 in the drive shaft 20.

The output or driving end of drive shaft 20 has a gear member 40 thereon. The gear member 40 may be integrally formed with the drive shaft 20, or may be separately formed and thereafter integrally connected to the end of drive shaft 20 so as to be coaxial with drive shaft 20. The drive shaft 20 is supported in input side rotary ball bearings 42, 44 which are mounted in the main housing member 10 (with their outer races in contact with an inner surface portion of main housing member 10). Bearings 42, 44 are separated by a washer 43. The gear 40 bears on the inner race 42a of the ball bearing 42 so as to rotate therewith, and the washer 30 bears on the inner race 44a of the ball bearing 44 so as to rotate therewith. In this manner, the drive shaft 20 is stably and securely rotatably supported in the bearings 42, 44 so as to be freely rotatable within the main housing member 10, with very low friction.

In the embodiment illustrated in the drawings, three planetary gear stages or gear units are shown as being sequentially arranged and interconnected in the main housing member 10. Each of the planetary gear stages is substantially identical. The first planetary gear stage comprises a first ring gear member 50 which is non-rotationally mounted in a recess or cavity 15 of the main housing member 10. Ring gear member 50 may be press fit in the housing member 10 or may otherwise be made non-rotational relative to the main housing member 10. For example, other arrangements to make ring gear 50 non-rotational in housing member 10 may comprise a projection or key, serrated mating surfaces, or the like. Also, ring gear 50 can be made non-rotational by pressure from threaded member 148 as will be described later. In the present embodiment, the ring gear member 50 has internal gear teeth 51 and serves as the fixed ring gear of the first planetary gear stage, and the gear 40 at the end of drive shaft 20 serves as the sun gear of the first planetary gear stage. Three planet gears 52, 53 and 54 are mounted between the fixed ring gear 50 and the sun gear 40, so as to rotate within the ring gear 50 responsive to rotation of sun gear 40. When the sun gear 40 rotates, the planet gears 52, 53, 54 rotate around the interior gear teeth of 51 of the fixed ring gear 50 and around the sun gear 40. A carrier 60 having shafts 62, 63, 64 press fit in respective bores therein is provided and is arranged such that the shafts 62, 63, 64 are mounted in interior openings or bores 52a, 53a and 54a, respectively, of the planet gears 52, 53 and 54. The planet gears 52, 53 and 54 are rotatable relative to the respective shafts 62, 63 and 64. Upon operation of the handpiece, rotation of the drive shaft 20 rotates the sun gear 40 which in turn causes the planet gears 52, 53, 54 to rotate around the sun gear 40 and around inner ring gear 50, and thereby causes the carrier 60 to rotate at the same speed (rpm) as the planet gears 52, 53, 54 rotate around the ring gear 50.

Attached fixedly to the output side of the carrier 60 is another gear 70 (similar to gear 40) which forms the sun gear of the second planetary gear stage or unit. A ring gear 80 (having internal gear teeth 81) is non-rotationally mounted in the interior of the main housing member 10, in a manner similar to fixed ring gear 50. Planet gears 72, 73, 74 are arranged between the sun gear 70 and the ring gear 80, and rotate around the ring gear 80 upon rotation of sun gear 70. A carrier 90, which is similar to the carrier 60, has shafts 92, 93, 94 extending therefrom and which are mounted in the interior bores or openings of the respective planet gears 72, 73 and 74 (see FIG. 4). The shafts 92, 93, 94 are preferably press fit into bores in the carrier 90. A sun gear 100 with a shaft 101 is mounted to the carrier 90 with the shaft 101 press fit into a bore 95 the carrier 90 such that the sun gear 100 is fixed relative to the carrier 90 and rotates with the carrier 90. The sun gear 70 is fixed to the carrier 60 in a similar manner by means of a shaft (not shown) integrally connected with the sun gear 70, the shaft (not shown) being press fit in a central bore (not shown) in carrier 60.

A third stage ring gear 110 with internal gear teeth 111 is non-rotationally mounted in the interior of the main housing member 10 in a manner similar to ring gears 50 and 80. Planet gears 122, 123, 124, similar to planet gears 52, 53, 54, are mounted in the ring gear 110, and are driven by the third stage sun gear 100. A carrier 130 with shafts 132, 133, 134 press fit thereon is provided such that the shafts 132, 133, 134 engage in bores of planet gears 122, 123, 124 so as to rotate around the sun gear 100 with rotation of planet gears 122, 123, 124 around the sun gear 100. An output shaft 140 has an end portion 141 which is press fit into a central bore 135 of carrier 130 and has a crown gear 142 which is press fit onto an output end portion of shaft 140. The crown gear 142 could be otherwise integrally formed with output shaft 140, as may be desired.

The output shaft 140 is supported within inner races of output side ball bearings 144, 146 which are mounted in a threaded member 148 which is threaded to the output end of the main housing member 10, as best seen in FIG. 2. The output section 11 is threaded to threads on the threaded member 148, also as seen in FIG. 2.

The threaded member 148 serves as a pressing member to retain the ring gears 50, 80 and 110 in the main housing member 10 such that the ring gears 50, 80, 110 are non-rotational relative to the main housing member 10. Therefore, even if the ring gears 50, 80, 110 are not physically press fit or otherwise physically made non-rotational relative to the housing member 10 (that is, they do not include serrations, keys or the like), the ring gears can be inserted into the recess or cavity 15 in main housing member 10, and the threaded member 148 is then threaded into the interior of main housing member 10 to tightly press the ring gears against shoulder 16 of main housing member 10, thereby maintaining them in fixed, non-rotational relationship relative to the main housing member 10. As mentioned above, other known means for making the ring gears non-rotational relative to the main housing member can be used. However, by using the above-described technique of locking or pressing the ring gears in place by means of the threaded member 148, a defective ring gear can be relatively easily replaced by disassembling the unit, by removing threaded member 148, and thereby easily removing the defective planetary gear unit and replacing it with a new one. After replacing a defective planetary gear unit, the device is reassembled and threaded member 148 is again threaded in place to press the ring gears against shoulder 16, thereby making the ring gears non-rotational relative to the main housing member 10.

A decorative ring 160 is provided near the output portion of the main housing member 10 which can be color coded to designate different output speeds for different dental handpieces or to designate different types of handpieces. The decorative ring 160 is retained between the main housing member 10 and the output section 11.

In the present invention, the multi-stage planetary gear system is designed so as to provide a 1:4 reduction in rotary speed at each stage thereof. The three-stage system described above therefore provides a total speed reduction ratio of 1:64. Therefore, a dental system with a 20,000 rpm input speed for the handpiece provides an ideal output speed of around 312 rpm (20,000÷64) at 40 psi of air pressure which operates the air pressure type vane motor of the standard type of dental drive unit. An electrical drive motor could be used in place of the air pressure type vane motor (or other type of pneumatic dental drive unit).

If a speed slower than about 300 or about 312 rpm is desired at the output of the handpiece, a further (fourth) planetary gear stage can be provided so as to provide an output speed of about 78 rpm for an input speed of around 20,000 rpm. Such a four stage planetary gear system will necessitate lengthening of the handpiece, which can be easily accomplished by providing a longer main handpiece section 10 with a recess or cavity 15 long enough to accommodate a fourth planetary gear stage.

For other dental uses, different reduction ratios may be desirable. For example, when performing implant operations, it is useful to use a two-stage planetary gear reduction handpiece which provides an overall 1:16 reduction in speed so that the output speed will be about 1250 rpm (for an input speed of about 20,000 rpm). In such a case, the main housing member may be made shorter (to accommodate only two planetary gear units), and the output shaft 140 would be connected to the center of the second stage carrier 60 so as to rotate therewith. Instead of making the main housing member 10 shorter to accommodate only two planetary gear stages, a spacer could be inserted in recess 15 and a longer output shaft could be used (or a longer input shaft could be used, depending on the location of the spacer).

An advantage of the arrangement of the present invention is that the planetary gear stages are sequentially arranged immediately adjacent to each other, with no bearing or support members therebetween. It is only required to provide bearings for the output shaft and for the input shaft, there being no need to provide any intermediate bearings within the planetary gear system per se. No bearing supports between planetary gear stages are required. This results in a compact, lighter, less expensive and more reliable overall operating system. Also, as described above, the unit can be repaired in a relatively simple manner by replacing either entire planetary gear. stages, or by replacing only parts of respective planetary gear stages, as may be required, by disassembly upon removal of threaded member 148.

The gears of each planetary gear unit in the illustrated embodiment are dimensioned and arranged so as to provide approximately a 1:4 rotational speed reduction ratio for each stage of the planetary gear system. Other dimensional configurations could be used so as to provide other gear reductions, as may be desired. However, a gear reduction of about 1:4 for each planetary gear stage (gear unit) has been found to provide a suitable high torque, low speed output which is particularly useful for rotationally driving endodontic files such as reamers, tapered files or other endodontic tapers for performing procedures such as root canal therapy, etc.

Each of the planetary gear stages in the illustrated embodiment comprises three planet gears. However, fewer than three planet gears can be used, and more than three planet gears can be used, depending upon specific system requirements. The number of shafts extending from the respective carriers is preferably the same as a number of planet gears.

While the invention has been described above with respect to a specific embodiment, it should be clear that various modification and alterations can be made within the scope of the appended claims.

What is claimed is:

1. A dental handpiece having a slow speed, high torque rotary output, comprising:

a housing member;

an input shaft rotatably mounted in said housing member, and having a coupling member at an input end portion thereof for being coupled to a rotary dental drive unit;

a plurality of speed reduction planetary gear stages sequentially arranged within said housing member, a first of said planetary gear stages being coupled so as to be rotationally driven by said input shaft;

subsequent planetary gear stages being sequentially coupled to each other such that an output of one planetary gear stage drives an input of a next subsequent planetary gear stage; and an output shaft coupled to a final output planetary gear stage of said plurality of sequentially arranged planetary gear stages, said output shaft providing a slow speed, high torque rotary output responsive to said input shaft being driven by a higher speed rotary dental drive unit.

2. The dental handpiece of claim 1, wherein each planetary gear stage provides a gear reduction of about 1:4.

3. The dental handpiece of claim 1, wherein each planetary gear stage comprises a central rotatable sun gear, an outer ring gear, and a plurality of planet gears engaged between said sun gear and said ring gear so as to rotate around said sun gear responsive to rotation of said sun gear, said ring gear being mounted to said housing member so as to be non-rotational relative to said housing member.

4. The dental handpiece of claim 3, wherein each planetary gear stage further comprises a carrier which is engaged with said plurality of planet gears so as to rotate relative to said ring gear along with said rotation of said planet gears around said sun gear, said carrier having a next stage sun gear mounted thereon which serves as the sun gear for the next subsequent planetary gear stage.

5. The dental handpiece of claim 4, further comprising:

a first bearing unit in said housing member for rotatably supporting said input shaft; and a second bearing unit in said housing member for rotatably supporting said output shaft.

6. The dental handpiece of claim 4, comprising three of said planetary gear stages sequentially coupled together.

7. The dental handpiece of claim 6, wherein each planetary gear stage provides a gear reduction of about 1:4.

8. The dental handpiece of claim 4, wherein said carrier has a plurality of shafts extending therefrom, said plurality of shafts being mounted in bores of respective planet gears such that said planet gears are rotatable relative to said shafts extending from said carrier.

9. The dental handpiece of claim 4, wherein said next stage sun gear mounted to said carrier is non-rotational relative to said carrier.

10. The dental handpiece of claim 3, comprising three of said planetary gear stages sequentially coupled together.

11. The dental handpiece of claim 10, wherein each planetary gear stage provides a gear reduction of about 1:4.

12. The dental handpiece of claim 1, comprising three of said planetary gear stages sequentially coupled together.

13. The dental handpiece of claim 12, wherein each planetary gear stage provides a gear reduction of about 1:4.

14. The dental handpiece of claim 1, wherein said output shaft has a drive gear at an output end thereof.

15. The dental handpiece of claim 14, further comprising:

a first bearing unit in said housing member for rotatably supporting said input shaft; and a second bearing unit in said housing member for rotatably supporting said output shaft.

16. A dental handpiece having a slow speed, high torque rotary output, comprising:

a housing member;

an input shaft rotatably mounted in said housing member, and having a coupling member at an input end portion thereof for being coupled to a rotary dental drive unit;

a first planetary gear unit mounted in said housing member, said first planetary gear unit including a first sun gear coupled to said input shaft so as to be rotationally driven by said input shaft, a first outer ring gear mounted in said housing member so as to be non-rotational relative to said housing member, and a plurality of first planet gears engaged between said first sun gear and said first ring gear so as to rotate around said first sun gear responsive to rotation of said first sun gear relative to said first ring gear;

a first carrier which is engaged with said plurality of first planet gears so as to rotate relative to said first ring gear along with said rotation of said first planet gears around said first sun gear;

a second planetary gear unit mounted in said housing member, said second planetary gear unit including a second sun gear coupled to said first carrier so as to be rotationally driven by said first carrier, a second outer ring gear mounted in said housing member so as to be non-rotational relative to said housing member, and a plurality of second planet gears engaged between said second sun gear and said second ring gear so as to rotate around said second sun gear responsive to rotation of said second sun gear relative to said second ring gear;

a second carrier which is engaged with said plurality of second planet gears so as to rotate relative to said second ring gear along with said rotation of said second planet gears around said second sun gear;

a third planetary gear unit mounted in said housing member, said third planetary gear unit including a third sun gear coupled to said second carrier so as to be rotationally driven by said second carrier, a third outer ring gear mounted in said housing member so as to be non-rotational relative to said housing member, and a plurality of third planet gears engaged between said third sun gear and said third ring gear so as to rotate around said third sun gear responsive to rotation of said third sun gear relative to said third ring gear;

a third carrier which is engaged with said plurality of third planet gears so as to rotate relative to said third ring gear along with said rotation of said third planet gears around said second sun gear;

an output shaft coupled to said third carrier so as to rotate with said third carrier, said output shaft providing a slow speed, high torque rotary output responsive to said input shaft being driven by a higher speed rotary dental drive unit.

17. The dental handpiece of claim 16, wherein each of said planetary gear units provides a gear reduction of about 1:4.

18. The dental handpiece of claim 16, wherein each of said carriers has a plurality of shafts extending therefrom, said plurality of shafts being mounted in bores of respective planet gears such that said respective planet gears are rotatable relative to said shafts extending from each of said carriers.

19. The dental handpiece of claim 16, wherein said output shaft has a drive gear at an output end thereof.

* * * * *

REEXAMINATION CERTIFICATE (3782nd)
United States Patent [19]
Meller et al.

[11] B1 5,569,034
[45] Certificate Issued Jun. 15, 1999

[54] DENTAL HANDPIECE PROVIDING LOW SPEED, HIGH TORQUE ROTARY OUTPUT USING PLURAL STAGE PLANETARY GEAR REDUCTION

[75] Inventors: Moshe Meller, Princeton; Michael Feldman, Toms River, both of N.J.

[73] Assignee: MTI Precision Products, Inc., Lakewood, N.J.

Reexamination Request:
No. 90/004,641, May 15, 1997

Reexamination Certificate for:
Patent No.: 5,569,034
Issued: Oct. 29, 1996
Appl. No.: 08/368,779
Filed: Jan. 4, 1995 08/368,779

[51] Int. Cl.⁶ ............................... A61C 1/02; A61C 1/08; A61C 1/18
[52] U.S. Cl. .............................................. 433/105
[58] Field of Search .................................. 433/105, 114

[56] References Cited

U.S. PATENT DOCUMENTS

| | | |
|---|---|---|
| 3,349,490 | 10/1967 | Lieb et al. ............ 433/105 |
| 4,040,311 | 8/1977 | Page, Jr. et al. ........ 433/105 |
| 4,433,957 | 2/1984 | Nakanishi ............. 433/105 |
| 5,281,138 | 1/1994 | Rosenstatter .......... 433/105 |

FOREIGN PATENT DOCUMENTS

| | | |
|---|---|---|
| 60-63310 | 5/1985 | Japan. |
| 2-130443 | 10/1990 | Japan. |

*Primary Examiner*—Nicholas D. Lucchesi

[57] ABSTRACT

A dental handpiece having a slow speed, high torque rotary output, comprises a housing member; an input shaft rotatably mounted in the housing member; a coupling member at an end portion of the input shaft for being coupled to a rotary dental drive unit; a plurality of planetary gear stages sequentially arranged within the housing member, a first of the planetary gear stages being coupled so as to be rotationally driven by the input shaft; subsequent planetary gear stages being sequentially coupled to each other such that an output of one planetary gear stage drives an input of a next subsequent planetary gear stage; and an output shaft coupled to a final output planetary gear stage of the plurality of sequentially arranged planetary gear stages. The output shaft provides a slow speed, high torque rotary output responsive to the input shaft being driven by a higher speed rotary dental drive unit.

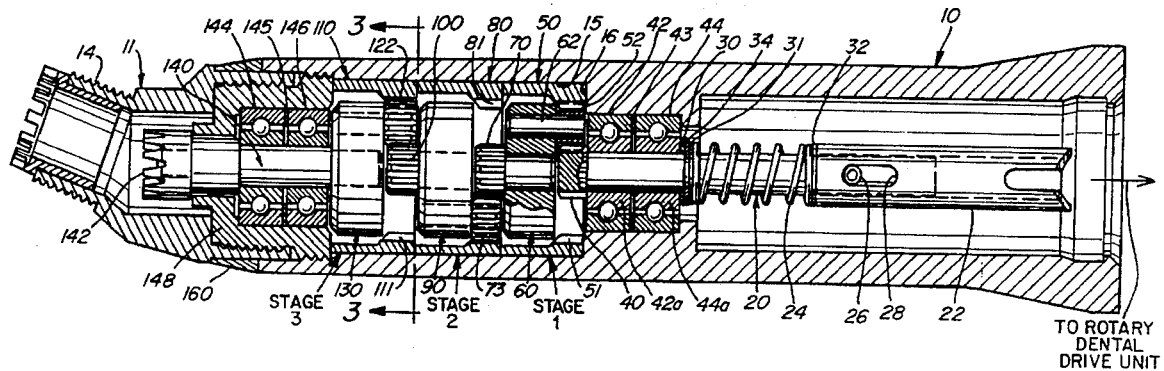

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–19 are cancelled.

* * * * *